United States Patent
Dittrich

(10) Patent No.: US 10,850,035 B2
(45) Date of Patent: Dec. 1, 2020

(54) AUTO-INJECTOR DEVICE

(71) Applicant: Sanofi-Aventis Deutschland GMBH, Frankfurt am Main (DE)

(72) Inventor: Marcus-Meinolf Dittrich, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 133 days.

(21) Appl. No.: 15/778,469

(22) PCT Filed: Nov. 21, 2016

(86) PCT No.: PCT/EP2016/078245
§ 371 (c)(1),
(2) Date: May 23, 2018

(87) PCT Pub. No.: WO2017/089257
PCT Pub. Date: Jun. 1, 2017

(65) Prior Publication Data
US 2018/0344929 A1  Dec. 6, 2018

(30) Foreign Application Priority Data

Nov. 27, 2015 (EP) .................................... 15196672

(51) Int. Cl.
*A61M 5/20* (2006.01)
*A61M 5/315* (2006.01)

(52) U.S. Cl.
CPC ............ *A61M 5/20* (2013.01); *A61M 5/3157* (2013.01); *A61M 2205/581* (2013.01); *A61M 2205/582* (2013.01); *A61M 2205/583* (2013.01); *A61M 2205/584* (2013.01)

(58) Field of Classification Search
CPC .................. A61M 5/20; A61M 5/3157; A61M 2205/584; A61M 2205/581; A61M 2205/582; A61M 2205/583; A61M 5/31525; A61M 5/31533; A61M 2005/3125; A61M 2005/3126
See application file for complete search history.

(56) References Cited

U.S. PATENT DOCUMENTS

| 8,652,100 B1 | 2/2014 | Cowe | |
| 2012/0310169 A1* | 12/2012 | Sonderegger | A61M 5/16813 604/189 |
| 2013/0204196 A1* | 8/2013 | Roberts et al. | A61M 5/3202 604/197 |

FOREIGN PATENT DOCUMENTS

| WO | WO 2010/066592 | 6/2010 |
| WO | WO 2012/117255 | 9/2012 |

OTHER PUBLICATIONS

PCT International Preliminary Report on Patentability in International Appln. No. PCT/EP2016/078245, dated May 29, 2018, 6 pages.

(Continued)

*Primary Examiner* — Amber R Stiles
(74) *Attorney, Agent, or Firm* — Fish & Richardson P.C.

(57) ABSTRACT

An injection device comprises an injector body having at least one indicator aperture; a medicament reservoir disposed within the injector body; a piston; and one or more status indicators. A movement of the piston expels a medicament out of the medicament reservoir, and operates to move at least one of the one or more status indicators relative to a corresponding indicator aperture.

13 Claims, 3 Drawing Sheets

(56) References Cited

OTHER PUBLICATIONS

PCT International Search Report and Written Opinion in International Appln. No. PCT/EP2016/078245, dated Feb. 13, 2017, 8 pages.

* cited by examiner

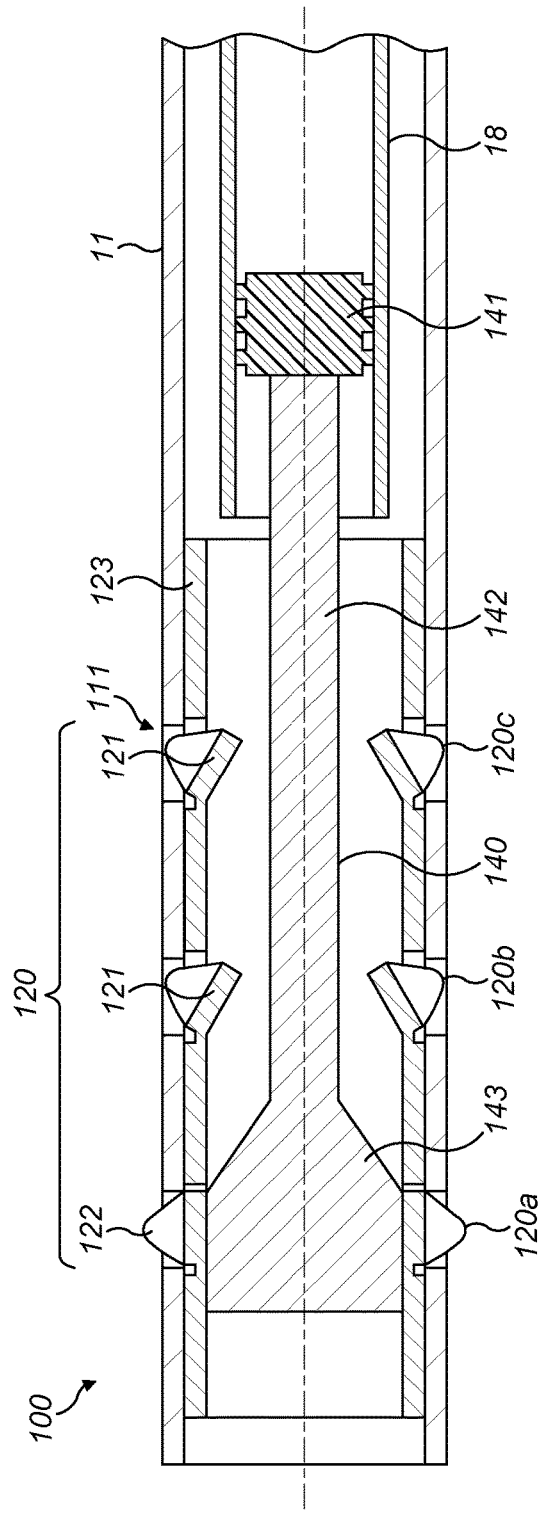
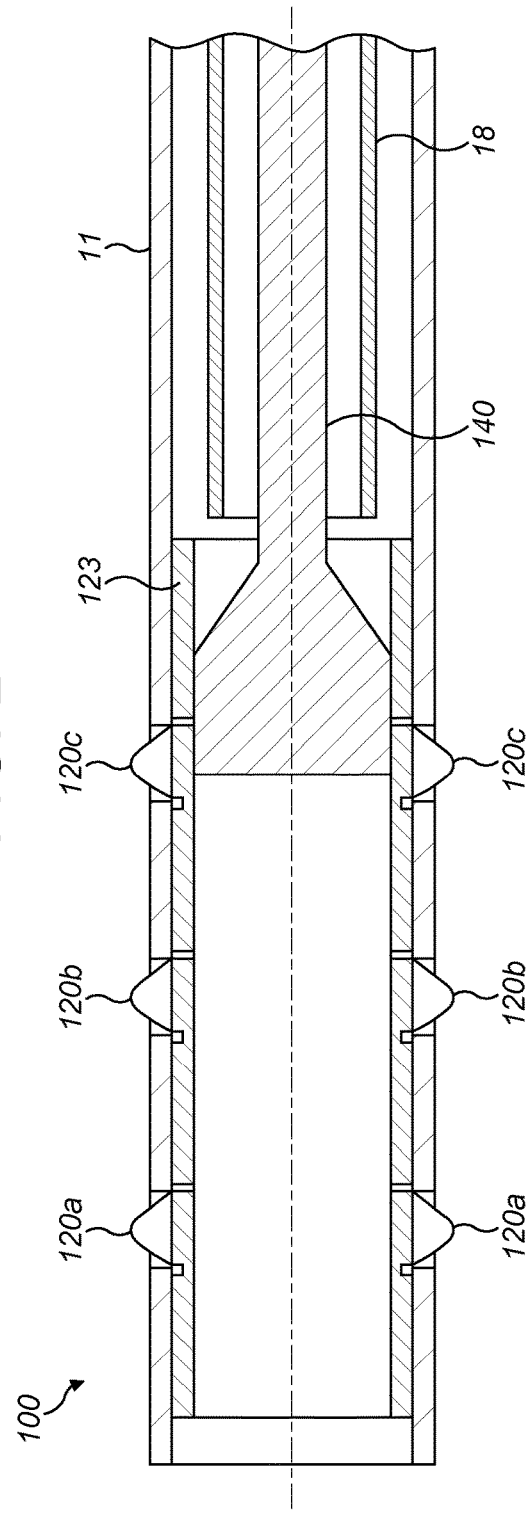
FIG. 2
FIG. 3

AUTO-INJECTOR DEVICE

CROSS REFERENCE TO RELATED APPLICATIONS

The present application is the national stage entry of International Patent Application No. PCT/EP2016/078245, filed on Nov. 21, 2016, and claims priority to Application No. EP 15196672.8, filed in on Nov. 27, 2015, the disclosures of which are incorporated herein by reference.

TECHNICAL FIELD

The present disclosure relates to an auto-injector device.

BACKGROUND

Injection devices, such as auto-injectors, are known in the art for dispensing a medicament to an injection site of a user. In particular, auto-injectors have been developed to enable laypersons to perform self-injections or injections on persons for which care is provided in a home care setting.

An auto-injector can be held against the injection site of a user and automatically injects a medicament into an injection site of a patient. Mechanical auto-injectors comprise springs or other mechanisms as a mechanical energy storage which drives a mechanism for displacing the medicament out of the reservoir into the patient's injection site.

Such injection devices can be needle based or needle free, and dispense the medicament when a trigger is activated. The trigger can be a button that is pressed by the user to start the injection. Alternatively, the trigger may be implemented as a depressible sleeve surrounding the needle or the medicament outlet, which sleeve is moved at least partly inside the injector housing when the user pushes the injector against the skin at the injection side. There are needle based injection devices in which the needle insertion into the patient's skin is performed manually by the user pressing the injection device against the skin at the injection site. In other injection device, the insertion of the needle into the skin takes place automatically as part of the injection automatic injection sequence.

The injectable medicaments may be based on drug formulations which have viscosities higher than the viscosity of water. In some embodiments, medicaments of various viscosities can be injected. For example, viscosity could range from about 3 to about 50 cP. In other embodiments, viscosity could be less than about 3 cP or greater than about 50 cP. Injection can further include delivering a medicament to a sub-cutaneous, an intra-muscular, or a transdermal location within a patient's body. The medicament can be in the form of a liquid, gel, slurry, suspension, particle, powder, or other type. In some cases, the viscosity may be temperature dependent and decrease with rising temperature. For instance, formulations in the field of Biologics are known to have such properties.

Devices of this type, as well as the medicament that they deliver, are commonly stored at relatively low ambient temperatures immediately before use. The medicament may, for example, be stored in a refrigerator at about 4° C. Injecting a liquid medicament at about 4° C. into the body can cause discomfort for the patient.

Further, the drive mechanism in some auto-injector devices may have mechanical energy storages like pre-loaded springs or gas expansion based systems that change energy output based on their temperature. As described above, it may be a mechanical spring based mechanism. Alternatively, the drive mechanism may for instance include an electric motor and a gear mechanism that causes the piston to move for displacing the medicament into the user. Alternatively, the drive mechanism may be a gas or fluid pressure operated mechanism, in which case the piston driving energy source is either a reservoir of pressurised gas or a chemical system in which two or more chemicals are mixed together to produce gas or fluid pressure.

The temperature dependent viscosity of the medicament or temperature dependent effects on the drive mechanism may change, e.g. prolong, the injection time significantly if the temperature is lower than prescribed, e.g., in cases where the user forgets to allow the injection to assume room temperature before performing the injection.

If the auto-injector is removed before the delivery is complete the medicament dosage may be incorrect, therefore an auto-injector may include a window for the user to observe the injection progress and to verify that all of the medicament has been injected, or may provide a click sound when the delivery is complete. It may be difficult to observe the progress of the ongoing injection sequence or verify that all of the medicament has been dispensed if a chosen injection site requires holding the auto-injector at an angle from which the window is not observable, or if the user is visually or hearing impaired.

SUMMARY

According to an aspect, an injection device is provided including an injector body having at least one indicator aperture, a medicament reservoir disposed within the injector body, a piston and one or more status indicators. A movement of the piston expels a medicament out of the medicament reservoir and operates to move at least one of the one or more status indicators relative to a corresponding indicator aperture.

The injector body may have a longitudinal axis. The one or more status indicators may be pushed radially out of the injector body as the piston moves axially through the injector body.

At least one of the status indicators may be positioned such that it is pushed out of the injector body when all or substantially all of the medicament has been propelled out of the medicament cartridge.

One or more of the status indicators may be positioned to indicate that a predetermined amount of the piston movement is complete.

The piston may include a stopper disposed in the medicament cartridge to expel the medicament, a piston shaft extending out of the medicament cartridge, and a piston head configured to push the one or more status indicators out of the injector body.

The piston may include an actuating member which extends axially from the piston head. The actuating member may be arranged to be outside the medicament cartridge as the piston moves axially through the injector body.

The position of one or more of the status indicators may be axially aligned with the medicament cartridge.

Each status indicator may include a finger element which is pivotably mounted to extend radially into the injector body in a first position and to extend parallel to an internal surface of the injector body in a second position, and an elevated portion which projects from the finger element so as to pass through the corresponding indicator aperture when the finger element is in the second position. The movement of the piston may push the finger element from the first position to the second position.

Each finger element may be formed by one or more cuts through an inner sleeve which is disposed internally within the injector body, with an uncut portion joining each finger element to the inner sleeve as a hinge.

The status indicators may be formed from a flexible sheet which is deformed to bulge inwards into the interior of the injector body in a first position. The movement of the piston may push the flexible sheet to invert into a second position in which the flexible sheet is deformed to bulge outwards through the indicator aperture.

The injection device may include a medicament which is retained within the medicament reservoir and is arranged to be expelled by the movement of the piston.

One of the status indicators may be configured to produce an auditory signal or vibration when pushed through the at least one indicator aperture.

An auto-injector is provided may include the injection device and a dispense mechanism configured to move the piston through the indicator body when activated.

According to another aspect, a method of operating an injection device is provided, including moving a piston to expel a medicament out of a medicament reservoir in an injector body, and moving at least one of one or more status indicators relative to a corresponding indicator aperture in the injector body.

These and other aspects of the invention will be apparent from and elucidated with reference to the embodiments described hereinafter.

BRIEF DESCRIPTION OF THE FIGURES

Exemplary embodiments are described with reference to the accompanying drawings, in which:

FIG. 2 is a schematic cross-sectional side view of the FIGS. 1A and 1B injection device according to an exemplary embodiment;

FIG. 3 is a schematic cross-sectional side view of the injection device of FIG. 2;

DETAILED DESCRIPTION

Figure 1A:
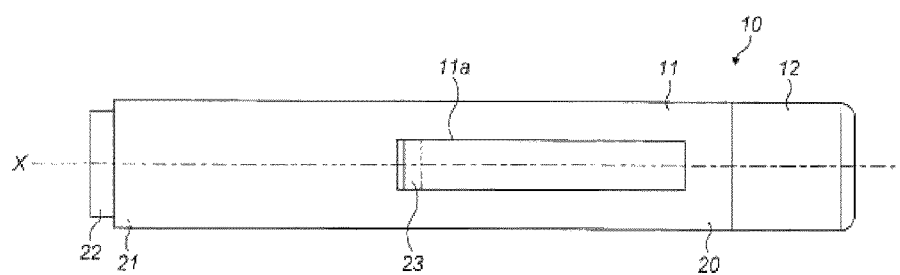
FIG. 1A is a schematic side view of an injection device according to an exemplary embodiment, with a cap attached to a body of the injection device.

An auto-injector device is provided which has a plurality of status indicators for indicating the current state of the injection process. The status indicators are located in apertures down the side of the injector body. The status indicators may be formed as finger elements which pivot within the apertures, or as a flexible sheet which is deformed to bulge through the apertures. In each embodiment, an element of each status indicator is forced outwards through the aperture by a piston of the syringe within the auto-injector as it dispenses the medicament.

The outwardly forced status indicators are visible to the user and may be brightly coloured to provide clear feedback on the status of the auto-injector. In addition, the status indicators protrude from the body of the device and so provide tactile feedback, which improves usability for a user who may be visually impaired. Upon being pushed outwards, the status indicators may produce a click sound as a further auditory or vibrational feedback.

A drug delivery device, as described herein, may be configured to inject a medicament into a patient. For example, delivery could be sub-cutaneous, intra-muscular, or intravenous. Such a device could be operated by a patient or care-giver, such as a nurse or physician, and can include various types of safety syringe, pen-injector, or auto-injector. The device can include a cartridge-based system that requires piercing a sealed ampule before use. Volumes of medicament delivered with these various devices can range from about 0.5 ml to about 2 ml. Yet another device can include a large volume device ("LVD") or patch pump, configured to adhere to a patient's skin for a period of time (e.g., about 5, 15, 30, 60, or 120 minutes) to deliver a "large" volume of medicament (typically about 2 ml to about 5 ml).

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device will often include a hollow needle ranging from about 25 to about 31 Gauge in size. Common sizes are 27 and 29 Gauge.

The delivery devices described herein can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions of an auto-injector may each be activated via an activation mechanism. Such an activation mechanism can include one or more of a button, a lever, a needle sleeve, or other activation component. Activation of an automated function may be a one-step or multi-step process. That is, a user may need to activate one or more activation components in order to cause the automated function. For example, in a one-step process, a user may depress a needle sleeve against their body in order to cause injection of a medicament. Other devices may require a multi-step activation of an automated function. For example, a user may be required to depress a button and retract a needle shield in order to cause injection.

In addition, activation of one automated function may activate one or more subsequent automated functions, thereby forming an activation sequence. For example, activation of a first automated function may activate at least two of needle insertion, medicament injection, and needle retraction. Some devices may also require a specific sequence of steps to cause the one or more automated functions to occur. Other devices may operate with a sequence of independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

Figure 1B:
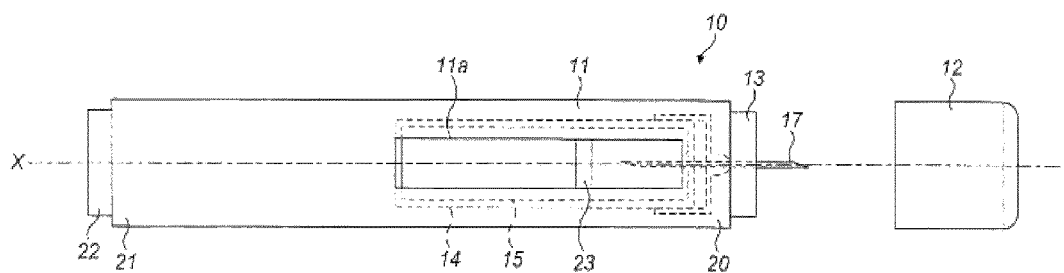
FIG. 1B is a schematic side view of the injection device of FIG. 1A, with the cap removed from the body.

According to some embodiments of the present disclosure, an exemplary drug delivery device 10 is shown in FIGS. 1A & 1B. Device 10, as described above, is configured to inject a medicament into a patient's body. Device 10 includes a housing 11 which typically contains a reservoir containing the medicament to be injected (e.g., a syringe) and the components required to facilitate one or more steps of the delivery process. Device 10 can also include a cap assembly 12 that can be detachably mounted to the housing 11. Typically a user must remove cap 12 from housing 11 before device 10 can be operated.

As shown, housing 11 is substantially cylindrical and has a substantially constant diameter along the longitudinal axis X. The housing 11 has a distal region 20 and a proximal region 21. The term "distal" refers to a location that is relatively closer to a site of injection, and the term "proximal" refers to a location that is relatively further away from the injection site.

Device 10 can also include a needle sleeve 13 coupled to housing 11 to permit movement of sleeve 13 relative to housing 11. For example, sleeve 13 can move in a longitudinal direction parallel to longitudinal axis X. Specifically, movement of sleeve 13 in a proximal direction can permit a needle 17 to extend from distal region 20 of housing 11.

Insertion of needle 17 can occur via several mechanisms. For example, needle 17 may be fixedly located relative to housing 11 and initially be located within an extended needle sleeve 13. Proximal movement of sleeve 13 by placing a distal end of sleeve 13 against a patient's body and moving housing 11 in a distal direction will uncover the distal end of needle 17. Such relative movement allows the distal end of needle 17 to extend into the patient's body. Such insertion is termed "manual" insertion as needle 17 is manually inserted via the patient's manual movement of housing 11 relative to sleeve 13.

Another form of insertion is "automated," whereby needle 17 moves relative to housing 11. Such insertion can be triggered by movement of sleeve 13 or by another form of activation, such as, for example, a button 22. As shown in FIGS. 1A & 1B, button 22 is located at a proximal end of housing 11. However, in other embodiments, button 22 could be located on a side of housing 11.

Other manual or automated features can include drug injection or needle retraction, or both. Injection is the process by which a bung or piston 23 is moved from a proximal location within a syringe (not shown) to a more distal location within the syringe in order to force a medicament from the syringe through needle 17. In some embodiments, a drive spring (not shown) is under compression before device 10 is activated. A proximal end of the drive spring can be fixed within proximal region 21 of housing 11, and a distal end of the drive spring can be configured to apply a compressive force to a proximal surface of piston 23. Following activation, at least part of the energy stored in the drive spring can be applied to the proximal surface of piston 23. This compressive force can act on piston 23 to move it in a distal direction. Such distal movement acts to compress the liquid medicament within the syringe, forcing it out of needle 17.

Following injection, needle 17 can be retracted within sleeve 13 or housing 11. Retraction can occur when sleeve 13 moves distally as a user removes device 10 from a patient's body. This can occur as needle 17 remains fixedly located relative to housing 11. Once a distal end of sleeve 13 has moved past a distal end of needle 17, and needle 17 is covered, sleeve 13 can be locked. Such locking can include locking any proximal movement of sleeve 13 relative to housing 11.

Another form of needle retraction can occur if needle 17 is moved relative to housing 11. Such movement can occur if the syringe within housing 11 is moved in a proximal direction relative to housing 11. This proximal movement can be achieved by using a retraction spring (not shown), located in distal region 20. A compressed retraction spring, when activated, can supply sufficient force to the syringe to move it in a proximal direction. Following sufficient retraction, any relative movement between needle 17 and housing 11 can be locked with a locking mechanism. In addition, button 22 or other components of device 10 can be locked as required.

With reference to FIG. 2, an auto-injector device 100 according to an exemplary embodiment is shown. The auto-injector 100 comprises an elongate injector body 11 having a medicament cartridge 18 disposed therein. The auto-injector may further comprise a needle (not shown) disposed at a distal end of the medicament cartridge 18 and a piston 140 disposed at the proximal end of the medicament cartridge 18. The auto-injector device 100 may further comprise a dispense button or sleeve trigger (not shown) and a dispense mechanism (not shown), substantially as described with respect to FIGS. 1a and 1b. The auto-injector device 100 may alternatively be a needle free device comprising an outlet nozzle (not shown).

When auto-injector device 100 is activated, the dispense mechanism causes the piston 140 to move axially towards the distal end of the medicament cartridge 18. The piston 140 according to the present embodiment comprises a stopper 141, a piston shaft 142 and a piston head 143. The stopper 141 is disposed within the medicament cartridge 18 and has substantially the same cross-section diameter as an inner cross section diameter of the medicament cartridge 18. The stopper 141 may be formed of a resilient rubber like material or may additionally have a rubber seal to improve contact and seal with the inner surface of the medicament cartridge 18. As the stopper 141 moves axially towards the distal end of the medicament cartridge 18, a medicament 16 within the cartridge is propelled or expelled out of the medicament cartridge 18 through the needle or outlet nozzle.

The piston shaft 142 is arranged to connect the stopper 141 at the distal end of the piston 140 and the piston head 143 at the proximal end of the piston 140. The piston shaft 142 extends out of the proximal end of the medicament cartridge 16. The cross-section of the piston shaft 142 has a smaller area than that of the medicament cartridge 18 and the stopper 141. Alternatively, the piston 140 has a constant cross section from the stopper 141 to the piston head 143.

The piston head 143 is disposed at the proximal end of the piston 140 and has substantially the same cross section diameter as an inner cross section diameter of the injector body 11. In some embodiments, only a portion of the piston head 143, e.g. a portion comprised of one or more flanges, extends from the piston shaft 142 toward the inner surface of the injector body 11.

The auto-injector 100 comprises a plurality of status indicators 120 arranged in one or more rows along the length of the injector body 11. The status indicators 120 are pivotably mounted to the injector body 11 so as to extend radially towards the interior of the injector body in a first position and lie flat against the interior surface of the injector body 11 in a second position. The injector body 11 is formed to have an indicator aperture 111 corresponding to each of the plurality of status indicators, wherein a portion of the status indicator 120 extends through the indicator aperture 111 to the exterior of the injector body 11 when the status indicator is in the second position. The status indicators 120 are arranged axially between a proximal point which is aligned with the piston head 143 before the auto-injector 100 is activated and a distal point which is aligned with the piston head 143 when the injection is completed.

The status indicators 120 according to the first embodiment comprise a finger element 121 attached to the injector body 11 by means of a hinge, which extends at an angle towards the interior of the injector body in a first position and extends parallel to the interior surface of the injector body in a second position. An elevated portion 122 projects from each finger element 121 and extends radially outwards through the indicator aperture 111 when the status indicator 120 is in the second position. The elevated portions 122 of the plurality of status indicators 120 may be a different colour to the external surface of the injector body 11.

The plurality of status indicators 120 further comprise connecting means in the form of an inner sleeve 123, which is a cylindrical structure arranged to fit inside the injector body 11 and lie flat against the interior surface of the injector body 11. The plurality of finger elements 121 are formed as part of the inner sleeve 123, for example, by cutting around each finger element 121 through a sheet material which forms the sleeve. A portion of the sheet material is left to form a hinge joining each finger element 121 to the inner sleeve 123, which is coupled to the interior surface of the injector body 11. The inner sleeve 123 is positioned such that the plurality of finger elements 121 and the corresponding elevated portion 122 for each finger element 121 is aligned with a corresponding indicator aperture 111.

The movement of the piston head 143 axially through the injector body 11 presses the plurality of status indicators 120 to lie flat against the interior surface of the injector body 11 in the second position. A leading edge of the piston head 143 is shaped to engage with the status indicators 120 and move the status indicators 120 from the first position to the second position. As each status indicator 120 is moved into the second position by the passage of the piston head 143, the elevated portion 122 of the status indicator 120 is moved radially out of the injector body 11 through the corresponding indicator aperture 111.

When auto-injector device 100 is activated, the dispense mechanism causes the piston 140 to move axially through the injector body 11 and the piston head 143 engages with each of the status indicators 120 arranged in a row in turn. Accordingly, as the piston head 143 progresses axially through the injector body 11, the status indicators 120 are moved in turn from the first position to the second position. As the medicament 16 is delivered by the dispense mechanism, the plurality of status indicators 120 are moved into the second position, such that the elevated portion 122 of each status indicator 120 extends out of the injector body 11. Here, there are two or more rows consisting of tines status indicators 120.

The status indicators 120 indicate the position of the piston head 143 as it moves axially through the injector body 11. The elevated portion 122 of each status indicator 120 is urged through the corresponding indicator aperture 111 when the piston head 143 passes behind that status indicator. The status indicators provide visual feedback for the user as they can be seen protruding from the outer surface of the injector body 11 and they can provide a contrasting colour element when activated. The status indicators 120 further provide tactile feedback as they can be felt by the user when they are protruding from the outer surface of the indicator body 11. In addition, the status indicators 120 may further comprising clicking means (not shown) configured to produce an auditory or vibrational signal when the status indicators 120 are moved into the second position.

With reference to FIG. 3, the auto-injector 100 of the first embodiment is shown in an activated state. The axial movement of the piston 140 through the medicament cartridge 18 is completed, and so delivery of the medicament 16 through the needle or outlet nozzle is complete. The three status indicators 120 in each row represent the progress on the injection when the dispense mechanism of the auto-injector 100 has been activated. Proceeding from the proximal end of a row of status indicators 120, a first status indicator 120a is arranged such that it is moved from the first position to the second position immediately upon activation of the dispense mechanism, by the first axial movement of the piston head 143. The first status indicator 120a provides feedback to the user that the dispense mechanism has been activated successfully and the injection is in progress.

A second status indicator 120b is positioned to indicate a halfway point in the injection process. The second status indicator 120b is arranged such that the piston head 143 passes the finger element 121 of the status indicator 120b when half of the medicament has been delivered. The second status indicator 120b provides feedback to the user that the dispense mechanism is working correctly and the medicament 16 is being delivered normally.

A third status indicator 120c is positioned to indicate completion of the injection, as shown in FIG. 3. When the stopper 141 of the piston 140 is located at the distal end of the medicament cartridge 18, the piston head 143 is positioned to move the finger element 121 of the third status indicator 120c to the second position. The third status indicator 120c provides feedback to the user that all of the medicament 16 has been dispensed from the medicament cartridge 18 and it is therefore safe to remove the needle from the injection site. In some embodiments, a status indicator 120c for indicating completion may be distinguished from other status indicators 120 by, for example, a different colour, a different shape of elevated portion 122, or a greater extent of protrusion from the injector body 11.

According to the first embodiment shown in FIG. 3, the plurality of status indicators 120 are configured to remain in the second position after being moved from the first position by the piston 140. The finger element 121 of each status indicator 120 may be held in position by a holding or locking mechanism or, alternatively, by a friction fit against the inner sleeve 123 or indicator aperture 111.

Figure 4:
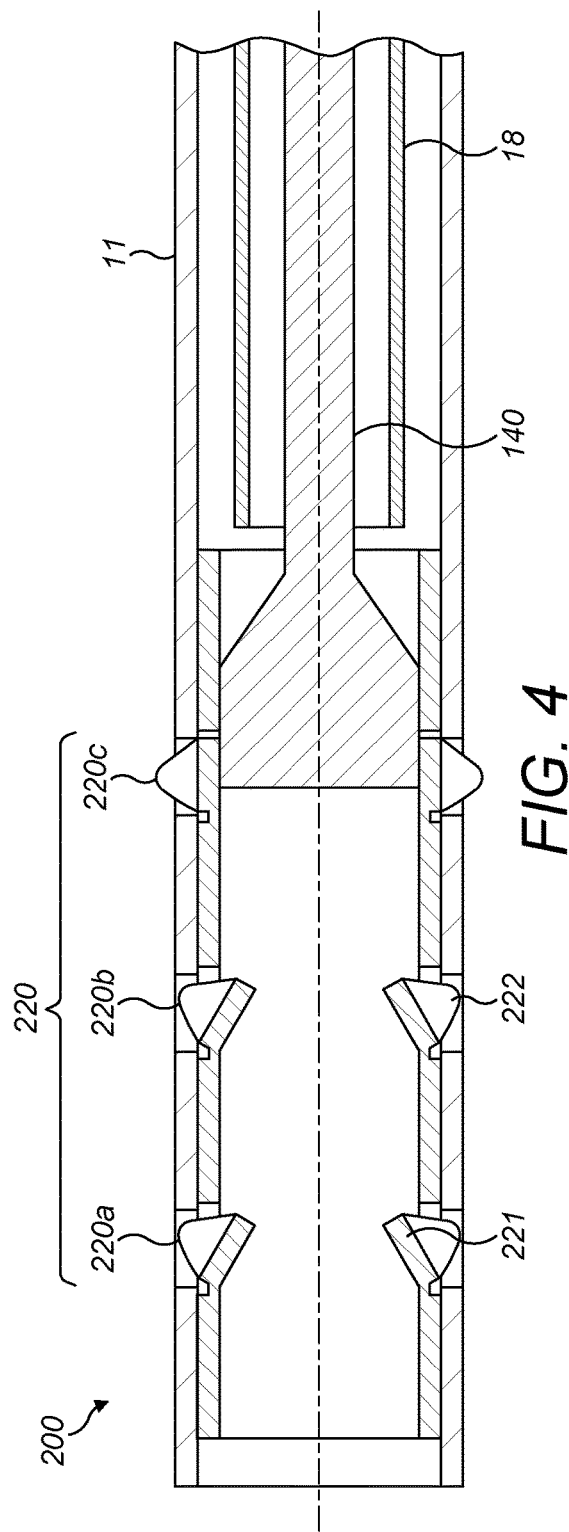
FIG. 4 is a schematic cross-sectional side view of the FIGS. 1A and 1B injection device according to an exemplary embodiment.

An auto-injector 200 according to a second embodiment is depicted in FIG. 4. According to the second embodiment, each status indicator 220 further comprises a biasing means which returns the finger element 221 from the second position to the first position in the absence of a force from the piston 140. As such, each status indicator 220 returns to the first position after the piston head 143 has moved axially past the status indicator 220. The completion of the injection is indicated by the protrusion of the elevated portion 222 of the third status indicator 220c only.

Figure 5:
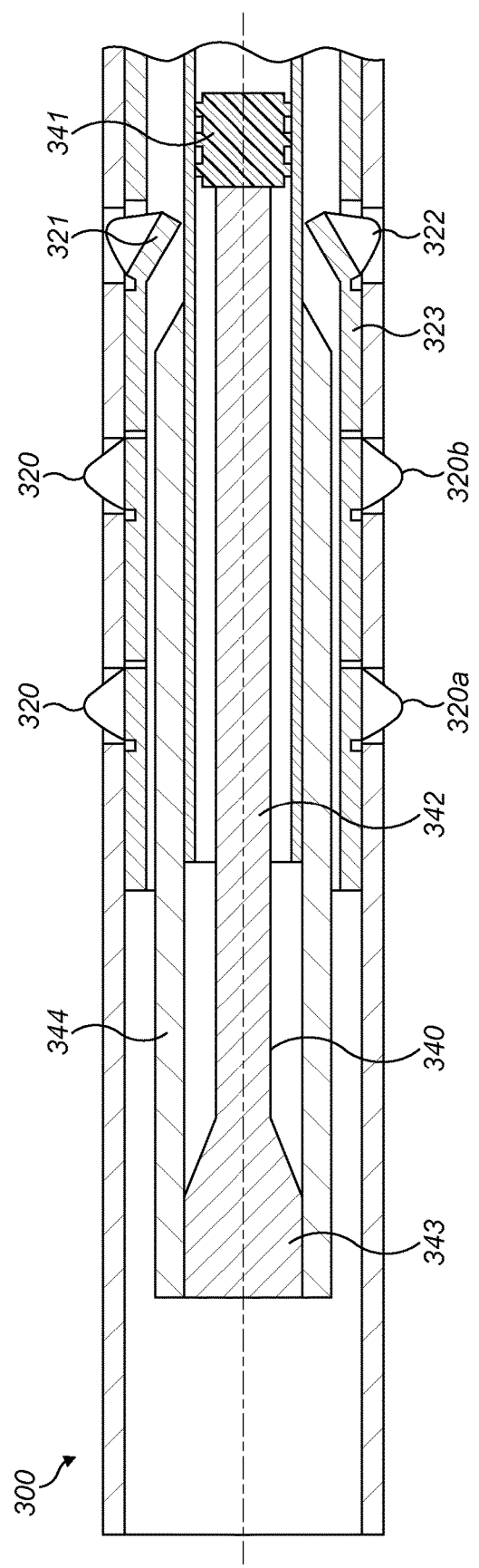
FIG. 5 is a schematic cross-sectional side view of the FIGS. 1A and 1B injection device according to an exemplary embodiment.

An auto-injector 300 according to a third embodiment is depicted in FIG. 5. According to the third embodiment, the piston 340 comprises a stopper 341, a piston shaft 342 and a piston head 343, substantially as described with respect to the first embodiment, and further comprises an actuating member 344 which extends axially from the piston head 343 in a distal direction.

The actuating member 344 is formed as a cylindrical outer sleeve having an outer diameter which is the same as the outer diameter of the piston head 343. That is, the outer diameter of the actuating member 344 as the same is the inner diameter of the inner sleeve 323 of the plurality of status indicators 320.

The actuating member 344 is arranged to extend in a distal direction from the leading edge of the piston head 343 between the housing 11 and the medicament chamber 18. The actuating member 344 forms a cylindrical sleeve disposed adjacent to the outer surface of the medicament chamber 18, and adjacent to the inner surface of the inner sleeve 323.

The indicators 320 are arranged axially between a proximal point which is aligned with the distal end of the actuating member 344 before the auto-injector 300 is activated and a distal point which is aligned with the distal end of the actuating member 344 when the injection is completed.

The movement of the actuating member 344 together with the piston 340 axially through the injector body 11 presses the plurality of status indicators 320 to lie flat against the interior surface of the injector body 11 in the second position. A leading edge of the actuating member 344 is shaped to engage with the status indicators 320 and move the status indicators 320 from the first position to the second position. As each status indicator 320 is moved into the second position by the passage of the actuating member 344, the elevated portion 322 of the status indicator 320 is moved radially out of the injector body 11 through the corresponding indicator aperture 111.

When auto-injector device 300 is activated, the dispense mechanism causes the piston 340 and the actuating member 344 to move axially through the injector body 11 and the actuating member 344 engages with each of the status indicators 320 arranged in a row in turn. Accordingly, as the actuating member 344 progresses axially through the injector body 11, the status indicators 320 are moved in turn from the first position to the second position. As the medicament 16 is delivered by the dispense mechanism, the plurality of status indicators 320 are moved into the second position, such that the elevated portion 322 of each status indicator 120 extends out of the injector body 11. Here, there are two or more rows consisting of three status indicators 320.

The status indicators 320 indicate the position of the actuating member 344 as it moves axially through the injector body 11. The elevated portion 322 of each status indicator 320 is urged through the corresponding indicator aperture 111 when the actuating member 344 passes behind that status indicator. The status indicators provide visual feedback for the user as they can be seen protruding from the outer surface of the injector body 11 and they can provide a contrasting colour element when activated. The status indicators 120 further provide tactile feedback as they can be felt by the user when they are protruding from the outer surface of the indicator body 11.

The indicators 320 are disposed at least partly alongside the medicament reservoir, and so a user can receive feedback when grasping the auto-injector device 300 at a point which is closer to the distal end of the device. This positioning is preferable to reduce the potential lever length, and hence, reduce the likelihood of moving the auto-injector device relative to the skin. Such movement may cause pain as it causes a sideways movement of the needle inside the skin.

With the indicators 320 disposed at the distal end of the device, the user is able to receive tactile feedback from the indicators 320 during and at the end of the injection while holding the device in a stable position.

In an alternative embodiment, the actuating member may be formed to include an aperture or a cutaway such that only the distal end of the actuating member engages with the status indicators and the actuating member engaged with only one of the status indicators at a time. As described with respect to the second embodiment, each status indicator may comprise a biasing means which returns the finger element from the second position to the first position in the absence of a force from the actuating member. As such, each status indicator returns to the first positioning after the distal end of the actuating member has moved axially past the status indicator. The completion of the injection is indicated protrusion of the elevated portion of the third status indicator only.

An auto-injector according to a fourth embodiment (not shown) comprises a plurality of status indicators arranged in one or more rows along the length of the injector body. The one or more status indicators each comprise a flexible sheet disposed at the corresponding indicator aperture, wherein the flexible sheet extends over the aperture. The flexible sheet is deformed to form a concave structure which extends into the interior of the injector body.

In some embodiments, the plurality of status indicators may be formed from an inner sleeve, which is a single flexible sheet formed into a cylinder to fit inside the injector body and lie flat against the interior surface of the injector body. Each status indicator is formed by a deformed area of the inner sleeve located at a corresponding indicator aperture.

The flexible sheet is in a first position when it is bulged inwards to protrude into the interior of the injector body, and can be inverted into a second position wherein it is bulged outwards to protrude out of the injector body through the indicator aperture. The flexible sheet forms a convex structure which extends out of the injector body when it is inverted into the second position.

When auto-injector device is activated, the dispense mechanism causes the piston to move axially through the injector body and the piston head engages with each of the status indicators arranged in a row in turn. Accordingly, as the piston head progresses axially through the injector body, the flexible sheet of each status indicator in turn is inverted from the first position to the second position. As the medicament is delivered by the dispense mechanism, the plurality of status indicators are moved into the second position, such that the flexible sheet of each status indicator forms a convex structure which extends out of the injector body.

The status indicators of the fourth embodiment indicate the passage of the piston head as it moves axially through the injector body. The flexible sheet of each status indicator is urged to invert through the corresponding indicator aperture when the piston head passes behind that status indicator. The status indicators provide visual feedback for the user as they can be seen protruding from the outer surface of the injector body and they can provide a contrasting colour element when activated. The status indicators further provide tactile feedback as they can be felt by the user when they are protruding from the outer surface of the indicator body. In addition, the status indicators may further comprising clicking means configured to produce an auditory or vibrational signal when the status indicators are moved into the second position.

Although a few embodiments have been shown and described, it will be appreciated by those skilled in the art that changes may be made in these embodiments without departing from the disclosure, the scope of which is defined in the appended claims. Various components of different embodiments may be combined where the principles underlying the embodiments are compatible. For example, in some embodiments, a single status indicator may be arranged to provide feedback that the dispense process has started or is completed. Alternatively, a plurality of status indicators may be arranged in one or more rows, or may be distributed around the surface of the indicator body in a regular pattern or with an irregular spacing. In some embodiments, the status indicators may comprise a finger element attached directly to the injector body to lie within the indicator aperture.

The dispense mechanism of an embodiment may be any suitable dispense mechanism. In some embodiments, the dispense mechanism includes a dispense button which activates a driving element to drive the rubber stopper through the medicament reservoir. The driving element may be, for example, a compressed coil spring, a compressed gas source, or an electric motor. The dispense mechanism may be a needle-less arrangement, which is configured to squirt a fine jet of liquid medicament at sufficient pressure to penetrate the skin at the injection site. The dispense mechanism may include a compressed gas source configured to expel the liquid medicament at a high pressure. The dispense mechanism may be activated automatically upon pushing a retractable sleeve completely into the housing, that is, by pressing the device against an injection site of the user.

In an alternative embodiment, an injection device is provided which is a manual injection device such as, for example, a syringe. A piston is pushed into the syringe by a user to expel a medicament through a needle at the distal end of the syringe. A plurality of status indicators, substantially as described with respect to the first embodiment or the second embodiment, are pushed into an activated position by the axial movement of the piston.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The term "drug delivery device" shall encompass any type of device or system configured to dispense a drug or medicament into a human or animal body. Without limitation, a drug delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, microneedle), inhaler (e.g., nasal or pulmonary), an implantable device (e.g., drug- or API-coated stent, capsule), or a feeding system for the gastro-intestinal tract. The presently described drugs may be particularly useful with injection devices that include a needle, e.g., a hypodermic needle for example having a Gauge number of 24 or higher.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a dug for at least one day (e.g., 1 to at least 30 days). In some instances, the chamber may be designed to store e drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refer to any substance which is sufficiently structurally similar to the original substance so as to have substantially similar functionality or activity (e.g., therapeutic effectiveness). In particular, the term "analogue" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, Including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu (B29) human insulin (insulin glulisine); Lys(B28), Pro(B29) human insulin (Insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); 829-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N—(N-lithocholyl-gamma-glutamyl)-des(B30) human insulin; B29-N-(ω-carboxyheptadecanoyl)-des(B30) human insulin and B29-N-(ω-carboxyhepta-decanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicitye), rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An example of an oligonucleotide is, for example: mipomersen sodium (Kynamro®), a cholesterol-reducing antisense therapeutic for the treatment of familial hypercholesterolemia.

Examples of DPP4 inhibitors are Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigens. The antibody can be polyclonal, monoclonal, recombinant, chimeric, de-immunized or humanized, fully human, non-human, (e.g., murine), or single chain antibody. In some embodiments, the antibody has effector function and can fix a complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrebodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present disclosure, which encompass such modifications and any and all equivalents thereof.

The invention claimed is:

1. An injection device comprising:
an injector body defining one or more indicator apertures;
a medicament reservoir disposed within the injector body;
a piston coupled to the medicament reservoir; and
one or more status indicators aligned axially with the one or more indicator apertures, respectively,
wherein the piston is configured to move axially through the injector body along a longitudinal axis of the injector body and relative to the one or more status indicators to expel a medicament out of the medicament reservoir and to push at least one status indicator of the one or more status indicators radially outward respectively into at least one indicator aperture of the one or more indicator apertures to position the at least one status indicator outside of the injector body while moving axially to expel the medicament, and
wherein at least one status indicator of the one or more status indicators is configured to produce an auditory signal or vibration when pushed through a respective indicator aperture of the one or more indicator apertures.

2. The injection device of claim 1, wherein d the one or more status indicators are disposed within an interior region of the injector body and are configured to pivot radially outward with respect to the longitudinal axis of the injector body and respectively into the one or more indicator apertures as the piston moves axially through the injector body.

3. The injection device of claim 1, wherein at least one status indicator of the one or more status indicators is positioned to be pushed outside of the injector body when all or substantially all of the medicament has been propelled out of the medicament reservoir.

4. The injection device of claim 1, wherein at least one status indicator of the one or more of status indicators is positioned to indicate that a predetermined amount of the piston movement is complete.

5. The injection device of claim 1, wherein the piston comprises:
a stopper disposed in the medicament reservoir for expelling the medicament;
a piston shaft extending out of the medicament reservoir from the stopper; and
a piston head coupled to the piston shaft and configured to push the one or more status indicators outside of the injector body.

6. The injection device of claim 5, wherein the piston further comprises an actuating member that extends axially from the piston head, and wherein the actuating member is arranged to be outside of the medicament reservoir as the piston moves axially through the injector body.

7. The injection device of claim 6, wherein at least one status indicator of the one or more status indicators is axially aligned with the medicament reservoir.

8. The injection device of claim 1, wherein each status indicator of the one or more status indicators comprises:
a finger element that is pivotably mounted to extend radially into the injector body in a first position and to extend parallel to an internal surface of the injector body in a second position; and
an elevated portion that projects from the finger element so as to pass through a respective indicator aperture of the one or more indicator apertures when the finger element is in the second position,
wherein a movement of the piston pushes the finger element from the first position to the second position.

9. The injection device of claim 8, wherein the finger element is defined by one or more cuts through an inner sleeve that is disposed internally within the injector body, with an uncut portion of the inner sleeve joining the finger element to a cylindrical body of the inner sleeve as a hinge.

10. The injection device of claim 1, wherein each status indicator of the one or more status indicators is defined by a flexible sheet that is deformed to provide the status indicator as an inner bulge that is directed radially inward into an interior region of the injector body in a first position of the status indicator, and wherein axial movement of the piston pushes the flexible sheet to invert the inner bulge into an outer bulge that passes through a respective indicator aperture of the one or more indicator apertures in a second position of the status indicator.

11. The injection device of claim 1, further comprising a medicament that is contained within the medicament reservoir and arranged to be expelled by axial movement of the piston.

12. An auto-injector, comprising:
an injector body defining one or more indicator apertures;
a medicament reservoir disposed within the injector body;
a piston coupled to the medicament reservoir;
one or more status indicators aligned axially with the one or more indicator apertures, respectively, wherein the piston is configured to move axially through the injector body along a longitudinal axis of the injector body and relative to the one or more status indicators to expel a medicament out of the medicament reservoir and to push at least one status indicator of the one or more status indicators radially outward respectively into at least one indicator aperture of the one or more indicator apertures to position the at least one status indicator outside of the injector body while moving axially to expel the medicament; and
a dispense mechanism configured to move the piston through the injector body when the dispense mechanism is activated,
wherein at least one status indicator of the one or more status indicators is configured to produce an auditory signal or vibration when pushed through a respective indicator aperture of the one or more indicator apertures.

13. A method of operating an injection device, the injection device comprising an injector body defining one or more indicator apertures, a medicament reservoir disposed within the injector body, a piston coupled to the medicament reservoir, and one or more status indicators respectively aligned axially with the one or more indicator apertures, the method comprising:
moving the piston axially through the injector body along a longitudinal axis of the injector body and relative to the one or more status indicators to expel a medicament out of the medicament reservoir; and while moving the piston axially to expel the medicament, pushing at least one status indicator of the one or more status indicators radially outward respectively into at least one indicator aperture of the one or more indicator apertures to position the at least one status indicator outside of the injector body, wherein the at least one status indicator produces an auditory signal or vibration when pushed through the at least one indicator aperture of the one or more indicator apertures.

\* \* \* \* \*